(12) United States Patent
Wardlaw (10) Patent No.: US 8,241,572 B2
(45) Date of Patent: *Aug. 14, 2012

(54) DISPOSABLE CHAMBER FOR ANALYZING BIOLOGIC FLUIDS

(75) Inventor: Stephen C. Wardlaw, Lyme, CT (US)

(73) Assignee: Abbott Point of Care, Inc., Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/206,636

(22) Filed: Aug. 10, 2011

(65) Prior Publication Data

US 2011/0294198 A1 Dec. 1, 2011

Related U.S. Application Data

(63) Continuation of application No. 12/774,445, filed on May 5, 2010.

(51) Int. Cl.
*G01N 33/00* (2006.01)
*G01N 21/75* (2006.01)
*G01N 31/22* (2006.01)
*G01N 33/52* (2006.01)
*B01L 3/00* (2006.01)
*B01L 99/00* (2010.01)

(52) U.S. Cl. ............. 422/73; 422/402; 422/500; 436/10

(58) Field of Classification Search .................... 422/73; 436/10

See application file for complete search history.

(56) References Cited

U.S. PATENT DOCUMENTS

| 3,447,863 A | 6/1969 | Patterson |
| 3,607,090 A | 9/1971 | Maxon |
| 3,879,106 A | 4/1975 | McCormick |
| 4,022,521 A | 5/1977 | Hall et al. |
| 4,171,866 A | 10/1979 | Tolles |
| 4,218,421 A | 8/1980 | Mack, Jr. |
| 4,264,560 A | 4/1981 | Natelson |
| 4,338,024 A | 7/1982 | Bolz et al. |
| 4,447,140 A | 5/1984 | Campbell et al. |

(Continued)

FOREIGN PATENT DOCUMENTS

GB 1049364 11/1966

(Continued)

OTHER PUBLICATIONS

EP Supplemental Search Report, Oct. 21, 2011.

*Primary Examiner* — Jill Warden
*Assistant Examiner* — Charles D Hammond
(74) *Attorney, Agent, or Firm* — O'Shea Getz P.C.

(57) ABSTRACT

An apparatus for analyzing biologic fluid is provided that includes first and second planar members, and at least three separators. At least one of the first planar member and second planar member is transparent. The separators are disposed between the planar members, and each individually has a height. The separators collectively having a mean height, and separate the planar members to form a chamber having a height extending between the planar members. At least one of the first planar member, second planar member, or separators is sufficiently deformable when the first planar member and second planar member are drawn toward each other by capillary force from a biologic fluid quiescently residing within the chamber to cause the mean chamber height to be substantially equal to the mean height of the separators.

14 Claims, 6 Drawing Sheets

U.S. PATENT DOCUMENTS

| | | |
|---|---|---|
| 4,883,642 A | 11/1989 | Bisconte |
| 4,950,455 A | 8/1990 | Smith |
| 5,039,487 A | 8/1991 | Smith |
| 5,096,836 A * | 3/1992 | Macho et al. ............ 436/169 |
| 5,321,975 A | 6/1994 | Levine et al. |
| 5,448,874 A | 9/1995 | Lemonnier |
| 5,547,849 A | 8/1996 | Baer et al. |
| 5,585,246 A | 12/1996 | Dubrow et al. |
| 5,726,751 A | 3/1998 | Altendorf |
| 5,812,312 A | 9/1998 | Lorinez |
| 5,837,547 A | 11/1998 | Schwartz |
| 6,004,821 A | 12/1999 | Levine et al. |
| 6,180,314 B1 | 1/2001 | Berndt |
| 6,197,593 B1 | 3/2001 | Deka et al. |
| 6,235,536 B1 | 5/2001 | Wardlaw |
| 6,252,660 B1 | 6/2001 | Frisch |
| 6,350,613 B1 | 2/2002 | Wardlaw et al. |
| 6,551,554 B1 | 4/2003 | Vermeiden et al. |
| 6,632,652 B1 | 10/2003 | Austin et al. |
| 6,667,177 B1 | 12/2003 | Yabusaki |
| 6,723,290 B1 | 4/2004 | Wardlaw |
| 6,866,823 B2 | 3/2005 | Wardlaw |
| 6,869,570 B2 | 3/2005 | Wardlaw |
| 6,929,953 B1 | 8/2005 | Wardlaw |
| 6,988,996 B2 | 1/2006 | Roe et al. |
| 7,179,423 B2 | 2/2007 | Bohm et al. |
| 7,850,916 B2 * | 12/2010 | Wardlaw ............ 422/73 |
| 2002/0135772 A1 | 9/2002 | Bornhop |
| 2003/0109059 A1 * | 6/2003 | Adrien et al. ............ 436/174 |
| 2004/0048330 A1 | 3/2004 | Bittner |
| 2007/0243117 A1 | 10/2007 | Wardlaw |
| 2009/0081773 A1 | 3/2009 | Kaufman |

FOREIGN PATENT DOCUMENTS

| | | |
|---|---|---|
| WO | 9624876 | 8/1996 |
| WO | 2005100539 | 10/2005 |

* cited by examiner

DISPOSABLE CHAMBER FOR ANALYZING BIOLOGIC FLUIDS

The present application is a continuation of U.S. patent application Ser. No. 12/774,445 filed May 5, 2010, which is a divisional of U.S. Pat. No. 7,850,916, which claims priority benefits under 35 U.S.C. §119(e) of U.S. Provisional Patent Application No. 60/560,307 filed Apr. 7, 2004, and PCT Patent Application No. PCT/US05/11602 filed Apr. 7, 2005, the disclosures of which are herein incorporated by reference.

BACKGROUND OF THE INVENTION

1. Technical Field

The present invention relates to chambers for analyzing biologic fluids in general, and to chambers that permit the enumeration of particulate matter within the biologic fluid in particular.

2. Background Information

The classic method of enumerating particles in a liquid medium, such as blood cells in whole blood or bacteria or other material in urine or other biologic fluid is the hemocytometer, which includes a chamber manufactured to a precise height and having visible ruled areas of precise dimension. The liquid containing the particles to be enumerated is introduced into the chamber. The liquid is diluted if necessary to reduce the number of particles to a manageable number. The operator then counts the number of particles in a given demarcated area. Since the area and height of the chamber are precisely known, the particle count per volume can be calculated. Although these chambers are generally ruled to demarcate a known area, this is not necessary if such a chamber is used in an image analyzer. With an image analyzer, rulings on the chamber itself are unnecessary because the field of view can be exactly calculated from the image.

Because they are precisely manufactured, hemocytometer chambers are relatively expensive and were not considered disposable. Modern precision plastics molding techniques have allowed the manufacture of some types of hemocytometer chambers at sufficiently low cost so as to be considered disposable in some instances, but chambers requiring substantial precision and/or thicknesses less than the traditional 0.1 mm are very difficult to mold accurately.

U.S. Pat. No. 4,950,455 describes a counting chamber formed from a rigid glass slide and a rigid glass coverslip with rigid particles, such as glass beads, contained therebetween. The beads maintain a thin spacing between the slide and coverslip, thereby forming the counting chamber.

Figure 1:
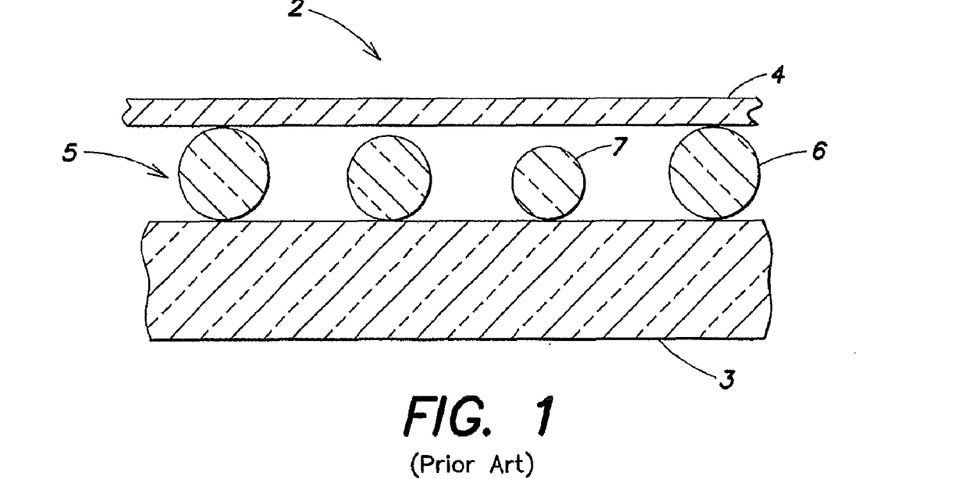
FIG. 1 is a cross-sectional schematic of the invention of the prior art, using a system in which all elements are rigid.
Figure 2:
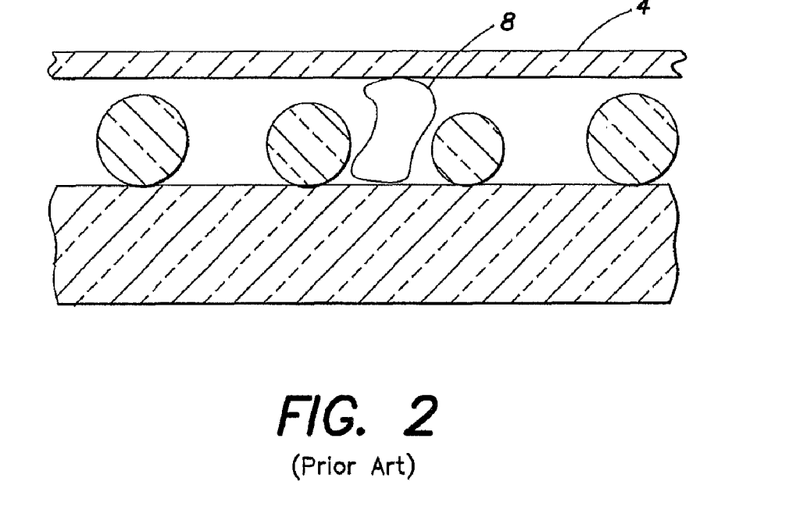
FIG. 2 is a cross-sectional schematic of the invention of the prior art, using a system in which all elements are rigid, and where particulate debris has been trapped.

A counting chamber formed from rigid upper and lower panels separated by rigid particles has substantial limitations, however. Referring to FIGS. 1 and 2, a prior art assembly generally denoted by 2 consists of a lower glass slide 3, an upper glass coverslip 4 and an entrapped layer formed from a plurality of glass beads 5. Because any microscopic beads are not completely uniform, having a coefficient of variation of the diameter of up to 10% or greater, the larger beads 6 "prop-up" the coverslip 4 to some extent, and the smaller beads 7 have no effect on the separation. The differences in bead diameter is a problem because while it is easy to determine and/or control the mean diameter of the beads, the spread of diameters is less well controlled, rendering the system less accurate than is desired. This results in a separation between the upper and lower layers of about the mean bead diameter plus one standard deviation. A greater problem is the presence of particulate debris as shown in FIG. 2. This debris can be present when the chamber is made or can be introduced by the environment or from a sample. The debris 8 can "prop up" the coverslip 4 and create a large area of increased volume in the chamber, which destroys its accuracy.

Another issue with this type of prior art chamber is that it is difficult to package a plurality of such disposables in an instrument used for automatically scanning and counting particles, such as an image analyzing system.

What is needed is an apparatus and method to overcome the limitations of the prior art, that provides a chamber for analyzing biologic fluids, including the enumeration of particulates within the fluid, which is inexpensive to produce, relatively insensitive to trapped particulate debris, and amenable to packaging for use in an automated test system.

SUMMARY OF THE INVENTION

According to the present invention, an apparatus for analyzing biologic fluid is provided that includes a first planar member, a second planar member, and at least three separators. At least one of planar members is transparent. The separators are disposed between the members, and separate the members to form a chamber having a height. At least one of the members or separators is sufficiently flexible to permit the chamber height to approximate the mean size of the separators. During use, the biologic fluid to be analyzed is disposed within the chamber.

According to one aspect of the present invention, each planar member is a tape that can be wound on a reel. In some embodiments, the planar members are initially attached to one another. In other embodiments, each planar member is initially separated from the other planar member.

According to one aspect of the present invention, a cassette is provided having at least one source reel and at least one take-up reel. The planar members are initially wound on a source reel, and are transferred to a take-up reel during operation of the apparatus. An analysis region is disposed between the source and take-up reels. The planar members pass through the analysis region during the operation of the apparatus.

There are numerous advantages associated the present invention. We discovered that if a counting chamber is produced using separators disposed between planar members, and if at least one the planar members and separators is flexible, the chamber behaves differently than the prior art devices, and the difference is highly advantageous. When a counting chamber is filled with a liquid, the capillary forces tend to pull the top and bottom planar members together, thus exerting a slight pressure on the retained separators. This pressure will cause the flexible element to deform in such a manner as to cause the chamber thickness to approximate, on average, the mean dimension of the separators disposed between the planar members. For example, if both top and bottom planar members are rigid and the separators are flexible, separators larger than the mean diameter will be compressed, and the planar members will approximate until more and more separators come into contact with the planar members, preventing further approximation. At that point, the height of the chamber approximates the average height of the separators and is readily ascertainable. In another example, if the separators are rigid and the top planar member is flexible, the top planar member will deform and be "tented-up" in a small area around each of the larger separators and be lower over smaller separators. The chamber will have an average height which closely approximates average separator height.

An advantage of the present invention is, therefore, that a chamber is formed having a volume that is accurately determinable because the height of the chamber is substantially uniform.

Another advantage of the present invention is that it can be manufactured in an inexpensive form and still provide the desired accuracy. The present invention does not require accurately machined voids or separators to accurately establish volume. Consequently, the invention can be manufactured inexpensively and still provide the desired accuracy. In addition, because it can be manufactured inexpensively, the present invention can practically be offered in a disposable form.

These and other objects, features and advantages of the present invention will become apparent in light of the detailed description of the invention provided below, and as illustrated in the accompanying drawings.

BRIEF DESCRIPTION OF THE DRAWINGS

The principles of the invention are further clarified by referring to the following figures, where.

DETAILED DESCRIPTION OF THE INVENTION

Referring to FIGS. 3-11, the present invention apparatus 10 for analyzing biologic fluid includes a first planar member 12, a second planar member 14, and at least three separators 16. At least one of planar members 12, 14 is transparent. The separators 16 are disposed between the members 12, 14, and separate the planar members 12, 14 to form a chamber 18 having a height 20. At least one of the members 12, 14 or separators 16 is sufficiently flexible to permit the chamber height 20 between the members 12, 14 to approximate the mean height of the separators 16.

The separators 16 can be any structure that is disposable between the planar members 12, 14, operable to space the planar members 12, 14 apart from one another. The dimension of a separator 16 that extends between the planar members is referred to herein as the height 22 of the separator 16. The heights 22 of the separators 16 typically do not equal one another exactly, but are within commercially acceptable tolerance for spacing means used in similar analysis apparatus. Spherical beads are an example of an acceptable separator 16 and are commercially available from, for example, Bangs Laboratories of Fishers, Ind., U.S.A.

In some embodiments, the separators 16 consist of a material that has greater flexibility than one or both of the first planar member 12 and the second planar member 14; i.e., relatively speaking, one or both of the planar members 12, 14 may be considered to be rigid relative to the separators 16 and the separators 16 may be considered to be flexible relative to one or both of the planar members 12, 14.

In other embodiments, the separators 16 consist of a material that has less flexibility than one or both of the first planar member 12 and the second planar member 14; i.e., relatively speaking, one or both of the planar members 12, 14 may be considered to be flexible relative to the separators 16 and the separators 16 may be considered to be rigid relative to one or both of the planar members 12, 14.

Subject to the flexibility characteristics described above, the planar members 12, 14 can be made from a variety of materials, provided at least one of the planar members 12, 14 is transparent. Transparent plastic films consisting of acrylic or polystyrene are examples of acceptable planar members 12, 14. Planar members 12, 14 in the form of a tape are particularly useful because they can be easily wound on a reel.

Figure 3:
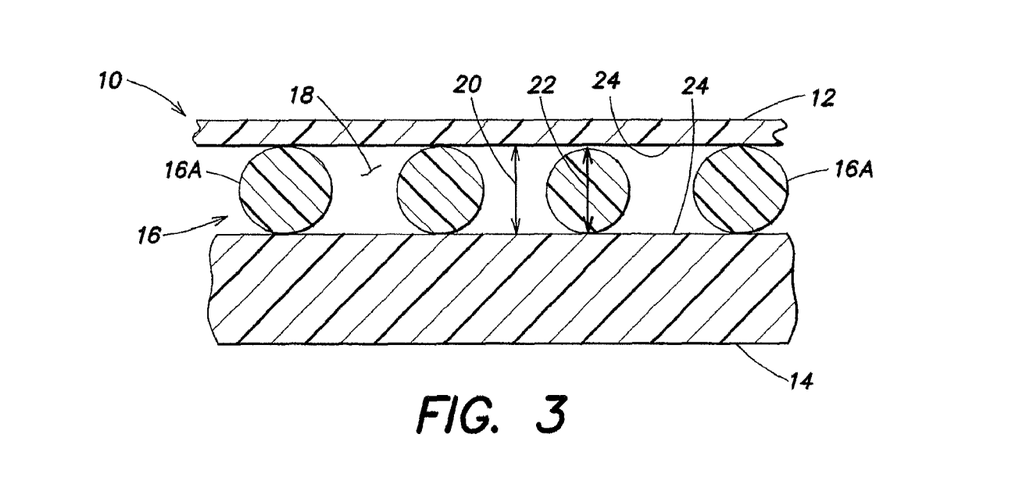
FIG. 3 is a cross-sectional schematic of the present invention, where the separators are flexible relative to the top and bottom planar members.

Now referring to FIG. 3, in an embodiment of the present invention 10 the first planar member 12 and the second planar member 14 are separated by a chamber 18 formed by plurality of separators 16 in the form of spherical beads. These beads 16 are formed from a material that has greater flexibility than the first planar member 12 and the second planar member 14; i.e., the planar members 12, 14 may be considered to be rigid relative to the beads 16 and the beads 16 may be considered to be flexible relative to the planar members 12, 14. Plastic beads 16 formed from polystyrene, polycarbonate, silicone and the like can be used. In this example, larger beads 16A are compressed to the point where the planar members 12, 14 have approximated to the point where most beads 16 are touching the interior surfaces 24 of the planar members 12, 14, thereby making the chamber height 20 just slightly less than the mean bead diameter.

Figure 4:
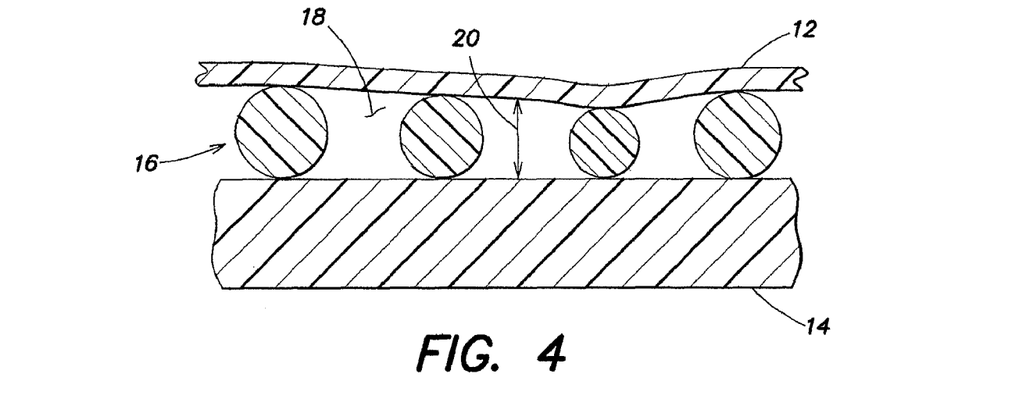
FIG. 4 is a cross-sectional schematic of the present invention, where the top planar member is flexible in relation to all other elements.

In FIG. 4, in another embodiment of the present invention 10 the first planar member 12 is formed from a material more flexible than the spherical beads 16 and the second planar member 14, and will overlay the beads 16 in a tent-like fashion, where the areas between the beads 16 are some arbitrary height determined by the bead diameters supporting that piece of the first planar member 12. Any transparent plastic film, such as acrylic, polystyrene, or the like will work provided it is thin enough to flex as shown. It should be apparent that in this circumstance, although small local areas will deviate from the desired chamber height 20, the average height of the chamber including the tented areas will be very close to that of the mean bead diameter. Our testing indicates that that the mean chamber height can be controlled to 1% or better at chamber heights of less than four microns using the present invention.

Figure 5:
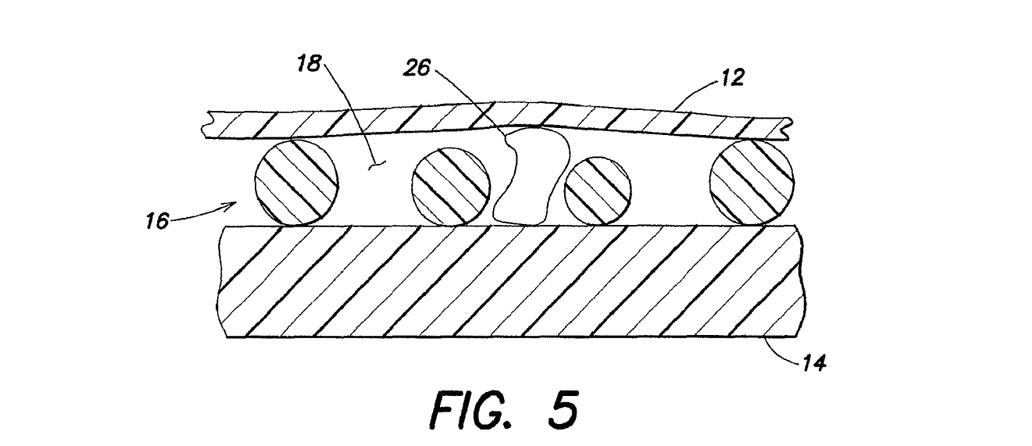
FIG. 5 is a cross-sectional schematic of the present invention, where the top planar member is flexible in relation to all other elements and where particulate debris has been trapped.

FIG. 5 shows the chamber 18 of FIG. 4 wherein a piece of particulate debris 26 has lodged. The first planar member 12 over the debris 26 has tented up, and the area under the debris 26 is of unknown height, but this disturbance only affects a small area of the chamber 18, as opposed to what would occur if the whole system was rigid.

Figure 6:
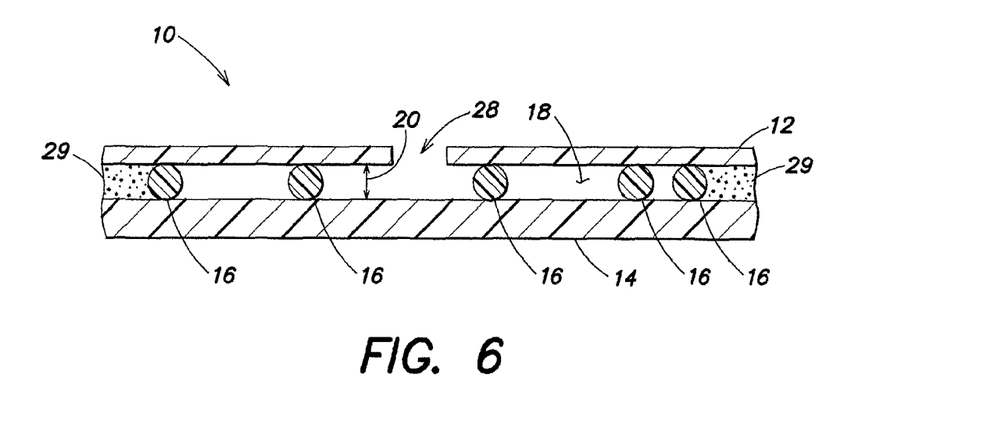
FIG. 6 is a schematic view of a first embodiment of the present invention.

FIG. 6 shows another embodiment of the invention 10, where the second planar member 14 is formed from a one inch wide strip of transparent plastic film (e.g., polyethylene terphthalate (PET)) of approximately fifty (50) microns in thickness, the first planar member 12 is formed from the same material as the second planar member 14 but in twenty-three (23) micron thickness, and the chamber 18 therebetween is formed from a plurality of plastic beads 16 with a mean diameter of four (4) microns. The first planar member 12 has an inner coating of a coloration agent, such as acridine orange, which will differentially color living white blood cells when examined with fluorescent illumination. Other reagents for fluorescence include astrozone orange, FITC, rhodamine and the like. Reagents which may be used with transmitted light to differentially color the white blood cells include astrozone orange, methylene blue, oxazine 170. The first planar member 12 includes a plurality of ports 28 (e.g., approximately three hundred (300) microns in diameter) punched at regular intervals, and the planar members 12, 14 are bonded at some points 29 between the ports 28 to form a series of separated analysis chambers 18.

This spacing between the two planar members 12, 14 in this embodiment is accomplished by spherical beads 16 of known and precisely controlled diameter (e.g., about four (4) microns in diameter). These beads 16 are randomly distributed on at least one of the planar members 12, 14 and can be attached as part of the reagent film containing the staining material. The material retaining the beads 16 should be such that they remain affixed to the planar member 12, 14 until at least after the fluid film movement has ceased so that they will not be swept away. An acceptable method of coating a film with beads 16 is to suspend the beads 16 in approximately a 0.5% solution of phytagel and apply a thin coating of the suspension by either spraying or meniscus coating. The optimum concentration of beads 16 will depend upon the type of bead and their method of manufacture, as well as the relative rigidity of the top and bottom planar members 12, 14. This concentration can be determined empirically on a batch-to-batch basis by applying a series of bead concentrations to the planar members 12, 14 to be used and then adding a liquid containing a dye, such as hemoglobin, which will give a useful optical density at the liquid layer thickness used. The average optical density of the liquid layer is then plotted against bead 16 density to determine the point where additional bead concentration produces no useful change in liquid layer thickness; i.e., the point where the chamber height 20 is substantially uniform. An alternate means of providing the separators is to negatively emboss one of the planar members 12, 14 with projections having approximately the same height of about four (4) microns, for example by laser-etching pits in a nip-roller and passing one planar member 12, 14 through the nip-roller assembly.

Figure 7:
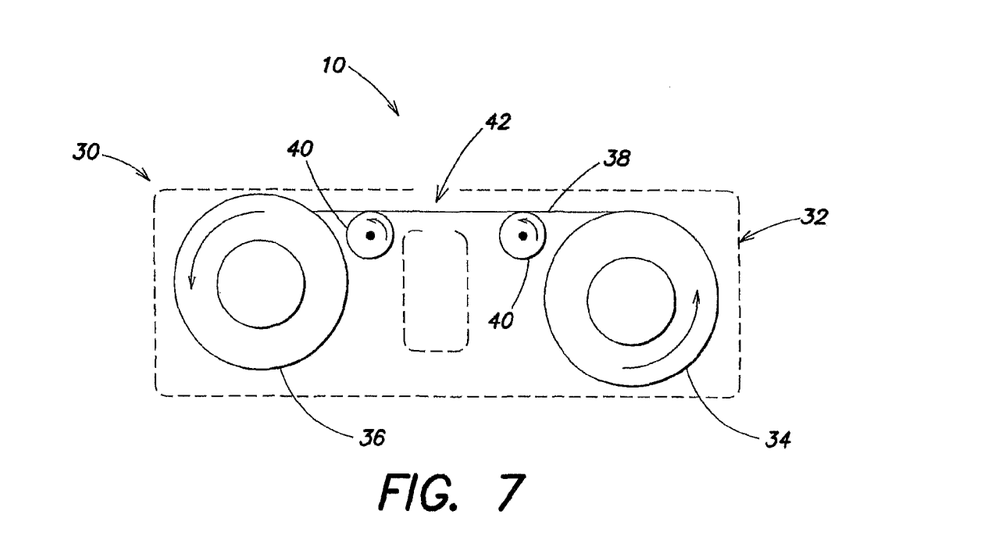
FIG. 7 is a schematic view of a cassette containing the first embodiment of the present invention.

FIG. 7 shows a cassette 30 having a shell 32 in which a source reel 34, a take-up reel 36, and a tape 38 extending therebetween are disposed. The "tape 38" is the embodiment of the present invention shown in FIG. 6 and described above. Initially, the tape 38 is wound on the source reel 34. Advancement of the tape 38 is controlled by rollers 40, which apply traction to the tape 38 at a point remote from the examination area 42 and can act to draw the tape 38 from the source reel 34 as required. The cassette 30 has a through-hole that allows an optical system to provide illumination through the tape 38.

Figure 8:
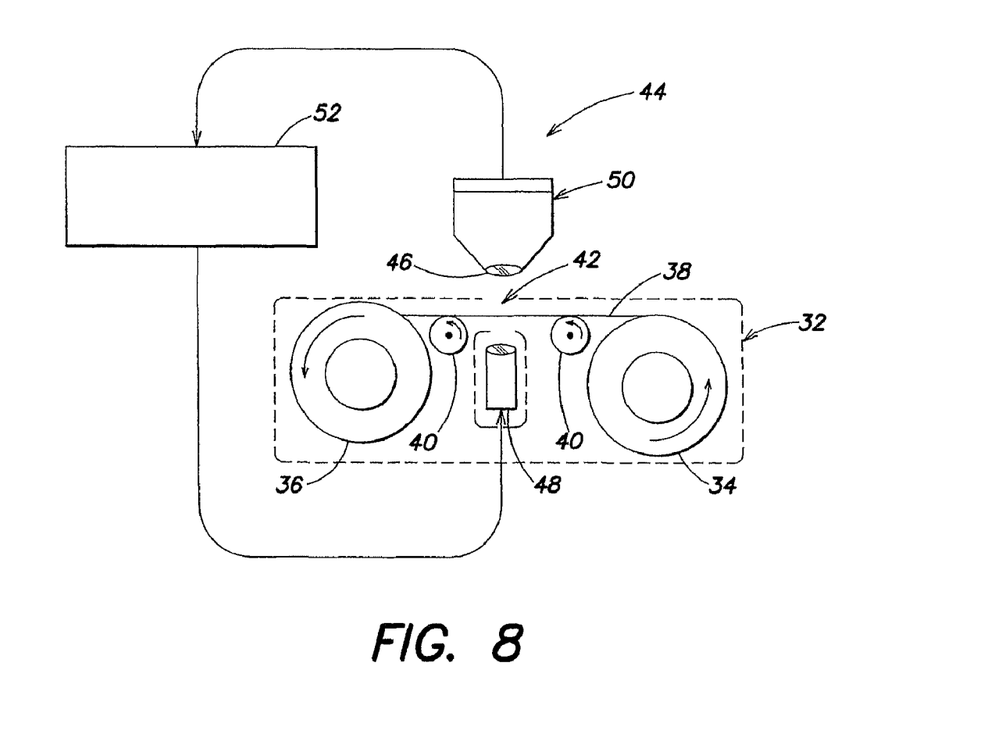
FIG. 8 is a schematic view of an instrument designed to utilize an embodiment of the present invention.

FIG. 8 shows an optical analysis system 44 containing the cassette 32. The optical analysis system 44, which consists of joined components including a lens 46, a variable-wavelength light source 48 and a CCD camera 50 are movable in three dimensions so as to allow the optical system 44 to focus upon the tape 38 in the examination area 42 and provide X-Y movement so as to allow scanning of the entire examination area 42, all under control of a system computer 52. Not shown is the sampling probe for extracting a biologic fluid (e.g., blood) from a sample tube and depositing a small drop on the tape 38. This sampling device can take the form of a tube-piercing or similar probe, which uses a stepping motor-driven syringe to extract and deposit biologic fluid samples. These devices are widely employed and well known to the art, and therefore will not be described further here.

Figure 9:
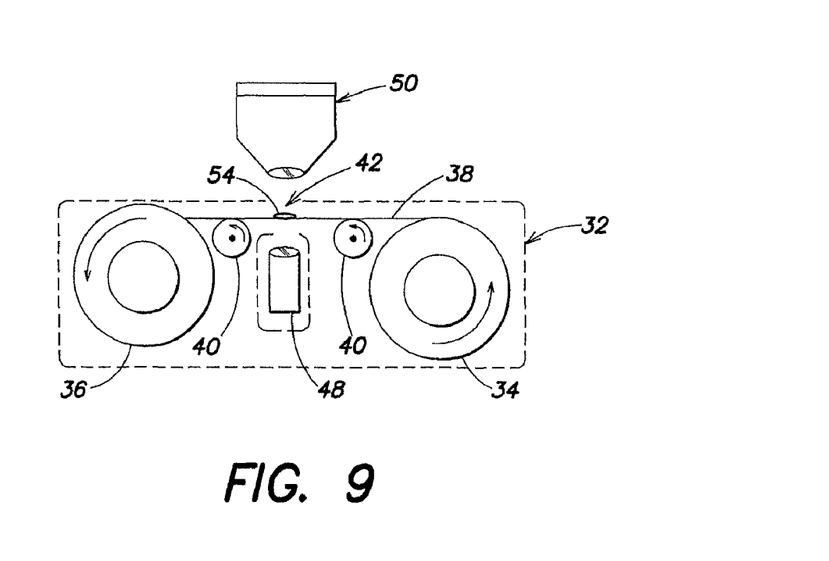
FIG. 9 is a schematic view of the instrument of FIG. 6 where the sample has been added to the planar member.

FIG. 9 shows the assembly of FIG. 8 just after a drop of biologic fluid 54 (e.g., blood) has been deposited into the sample entry port 28 (see FIG. 6) of a chamber 18 formed between the planar members 12, 14.

Figure 10:
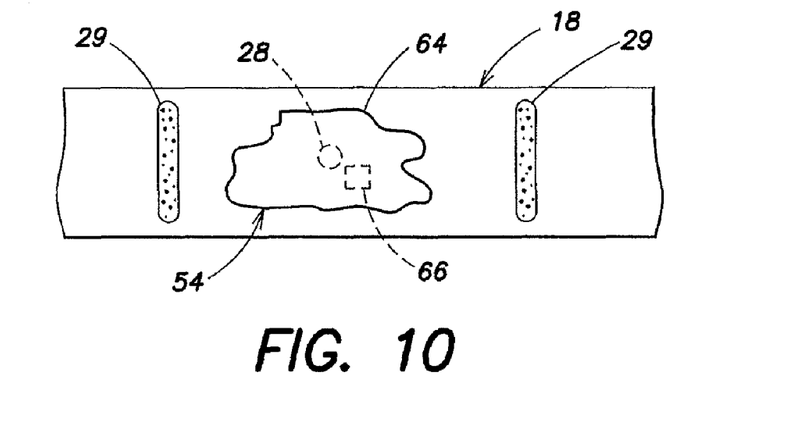
FIG. 10 is a schematic view of the sample after spreading out between the planar members.

FIG. 10 is a schematic view of the entire area of the sample film 64 of biologic fluid 54, which generally has an irregular border. In this example, the biologic fluid is blood. Because the white blood cells within the sample film 64 tend to become readily entrapped in the chamber 18, they are generally found in highest concentration within a few millimeters of the port 28.

Figure 11:
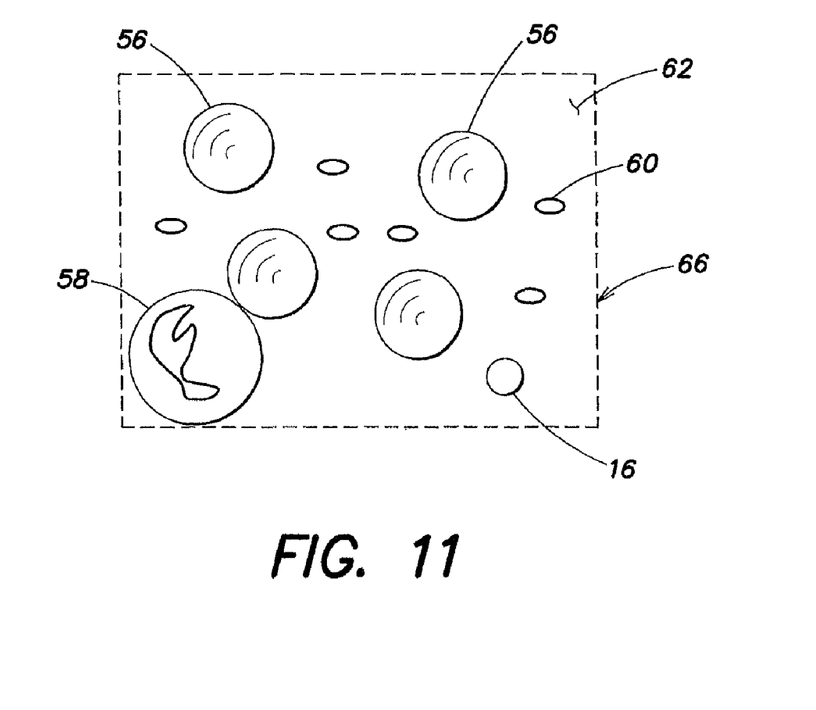
FIG. 11 is a schematic view of a typical field of view.

FIG. 11 is a schematic view of the analysis field 66 in FIG. 10, which, in the case of a whole blood sample, would show red blood cells 56, white blood cells 58, platelets 60, all surrounded by the blood plasma 62. The beads 16 are also seen but are readily distinguished from all other elements because of their size and refractive index.

The characterization of the white blood cells 58 (white blood cell differential count) is performed by the classification of each individual white blood cell 58 as it is encountered using either traditional image-processing methods or by the technique described in U.S. Pat. Nos. 5,321,975 and 6,350,613, both of which patents are hereby incorporated by reference. A number of supravital stains have been described which differentially color the different classes of white blood cells 58 as has been described in U.S. Pat. No. 6,235,536, which is also hereby incorporated by reference. Because the white blood cells 58 are slightly compressed and readily imaged, stored images of cells are viewable by the technologist in the case of questionable cell classifications.

As an example of the utility of this invention, the white blood cell 58 count of the sample film 64 may be performed by enumerating all of the white blood cells 58 found within the sample film 64 and dividing that number by the volume of the sample film 64. Although it is possible to deposit a specific amount of sample within the chamber 18, it is preferable to deposit an approximate amount and indirectly measure the volume. This can be done by mechanisms such as: 1) the volume of the drop of sample when first deposited can be calculated by interferometric imaging using optical techniques available from sources such as the Zygo Corporation of Middlefield, Conn. USA; or 2) the volume of sample following film formation is calculated by measuring the area of the film 64 and multiplying this by the average height of the film.

Figure 6A:
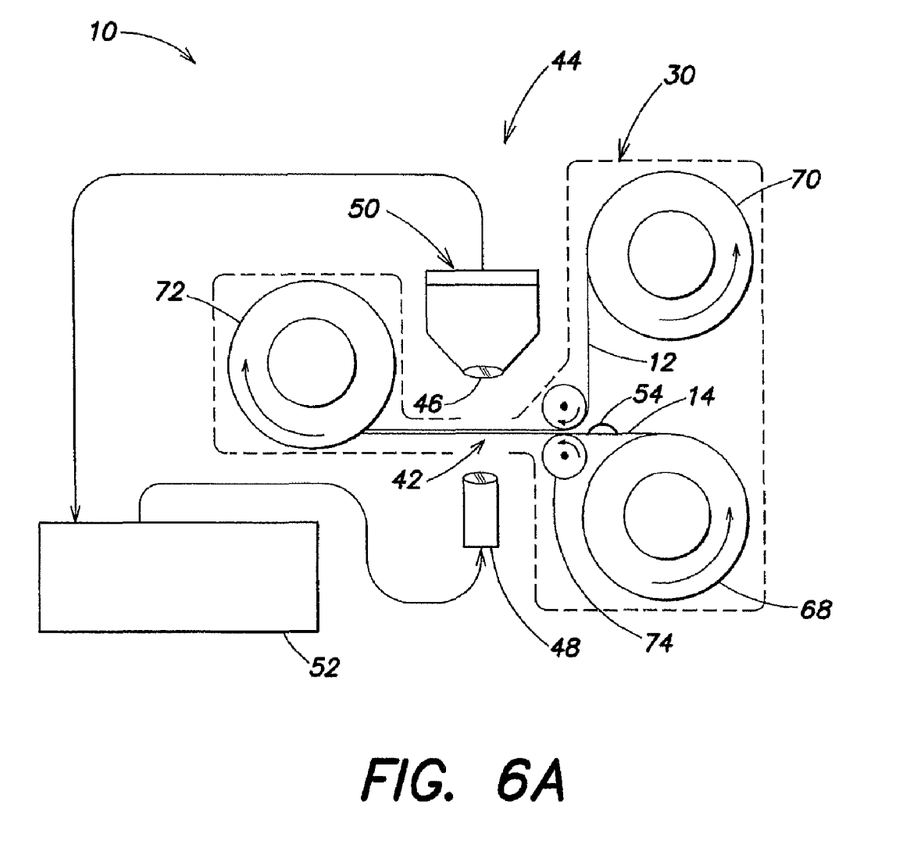
FIG. 6A is a schematic view of an instrument designed to utilize a second embodiment of the present invention.

FIG. 6A shows an optical analysis system 44 containing another embodiment of the present invention 10 that includes a cassette 30 in which a second planar member reel 68, first planar member reel 70, and take-up reel 72. Advancement of the planar members 12, 14 is controlled by take-up nip-rollers 74, which apply traction to the combined planar members 12, 14 at a point remote from the examination area 42 and can act to draw the planar members 12, 14 from their reels 68, 70 as required. The optical analysis system 44, which consists of joined components including a lens 46, a variable-wavelength light source 48 and a CCD camera 50 are movable in three dimensions so as to allow the optical analysis system 44 to focus upon the joined planar members 12, 14 in the examination area 42 and provide X-Y movement so as to allow scanning of the entire examination area 42, all under control of a system computer 52. A drop of biologic fluid 54 (e.g., blood) is shown deposited onto the second planar member 14. The nip-rollers 74 are operable to advance the planar members 12, 14 to a point just past the nip-rollers 74, where the separators 16 disposed between the planar members 12, 14 are in contact with each planar member 12, 14, and the biologic fluid contacts the interior surface 24 of each planar member 12, 14 and spreads to form a thin sample film 64. The planar members 12, 14 are then advanced so as to be readable by optical analysis system 44.

Since the overall accuracy of the system 44 when using a method of volume calculation depends upon the accuracy of the chamber height 20, it may be expedient to use an internal standard means to calculate the exact chamber height 20. An example of an internal standard includes a flexible or flowable material which is not miscible with the sample and which contains a known, stable and uniform concentration of a sensible optical dye. The material can be dyed flexible beads, dyed oil or the like, and may be present in one or more areas of the chamber 18. Since the optical density is in direct proportion to the thickness of the calibrator material, measurement of the optical density of the part of the calibrator material which completely fills the chamber height 20 will allow the calculation of the exact chamber height 20 to within the precision capabilities of the optical system.

Although the most frequent use for such a chamber 18 will be for enumerating blood cells in whole blood, it is equally useful for examination of any undiluted fluid having sufficient particles to count. The chamber height 20 is not limited to the disclosed four microns but can be larger or smaller to accommodate different separator sizes and/or concentrations.

Although this invention has been shown and described with respect to the detailed embodiments thereof, it will be understood by those skilled in the art that various changes in form and detail thereof may be made without departing from the spirit and the scope of the invention.

What is claimed is:

1. An apparatus for analyzing biologic fluid, comprising:
    a first planar member;
    a second planar member, wherein at least one of the first planar member and second planar member is transparent; and
    at least three separators disposed between the planar members, each separator individually having a height and the separators collectively having a mean height, separating the planar members to form a chamber having a height extending between the planar members;
    wherein the separators are independent of the first planar member and second planar member, and are randomly distributed within the chamber; and
    wherein at least one of the first planar member, second planar member, or separators is sufficiently deformable when the first planar member and second planar member are drawn toward each other by capillary force from a biologic fluid quiescently residing within the chamber to cause the mean chamber height to be substantially equal to the mean height of the separators.

2. The apparatus of claim 1 wherein at least one of the first planar member and the second planar member comprise plastic.

3. The apparatus of claim 1 wherein both of the first planar member and the second planar member comprise plastic.

4. The apparatus of claim 3, wherein the first planar member has a greater deformability than the second planar member and the separators.

5. The apparatus of claim 1, wherein the separators are attached to at least one of the first planar member or the second planar member.

6. The apparatus of claim 1, wherein the number of separators randomly disposed in a given area of the chamber is such that additional separators of the same type do not appreciably change the chamber height within the area.

7. The apparatus of claim 1, wherein the separators within the chamber have a concentration, and the number of separators randomly disposed within the chamber is such that increasing the concentration does not appreciably change the chamber height.

8. The apparatus of claim 1, wherein the first planar member has an interior surface contiguous with the chamber, and the second planar member has an interior surface contiguous with the chamber, and the interior surfaces are substantially parallel with one another.

9. The apparatus of claim 8, wherein the separators are independent of the first planar member and second planar member, and the at least three separators are attached to one of the interior surfaces.

10. An apparatus for analyzing biologic fluid, comprising:
    a first planar member;
    a second planar member, wherein at least one of the first planar member and second planar member is transparent; and
    at least three separators disposed between the planar members, each separator individually having a height and the separators collectively having a mean height, separating the planar members to form a chamber having a height extending between the planar members;
    wherein the separators are independent of the first planar member and second planar member, and are randomly distributed within the chamber; and
    wherein the first planar member is sufficiently deformable when the first planar member and second planar member are drawn toward each other by capillary force from a biologic fluid quiescently residing within the chamber to cause the mean chamber height to be substantially equal to the mean height of the separators.

11. The apparatus of claim 10 wherein both of the first planar member and the second planar member comprise plastic.

12. The apparatus of claim 10, wherein the number of separators randomly disposed in a given area of the chamber is such that additional separators of the same type do not appreciably change the chamber height within the area.

13. An apparatus for analyzing biologic fluid, comprising:
    a first planar member;
    a second planar member, wherein at least one of the first planar member and second planar member is transparent; and
    at least three separators disposed between the planar members, each separator individually having a height and the separators collectively having a mean height, separating the planar members to form a chamber having a height extending between the planar members, and wherein the separators are randomly distributed within the chamber;
    wherein the first planar member is sufficiently deformable when the first planar member and second planar member are drawn toward each other by capillary force from a biologic fluid quiescently residing within the chamber to cause the mean chamber height to be substantially equal to the mean height of the separators.

14. The apparatus of claim 13, wherein the first planar member is sufficiently deformable when the first planar member and second planar member are drawn toward each other by capillary force from the biologic fluid quiescently residing within, which fluid does not completely fill the chamber.

* * * * *